(12) United States Patent
Bourrieres et al.

(10) Patent No.: US 7,438,237 B2
(45) Date of Patent: Oct. 21, 2008

(54) METHOD FOR IDENTIFICATION AND AUTHENTICATING WITHOUT SPECIFIC READER AN IDENTIFIER

(75) Inventors: Francis Bourrieres, Montauban (FR); Clement Kaiser, Montauban (FR)

(73) Assignee: Novatec SA, Montauben (FR)

( * ) Notice: Subject to any disclaimer, the term of this patent is extended or adjusted under 35 U.S.C. 154(b) by 364 days.

(21) Appl. No.: 10/530,093

(22) PCT Filed: Dec. 10, 2003

(86) PCT No.: PCT/FR03/03668

§ 371 (c)(1),
(2), (4) Date: Apr. 1, 2005

(87) PCT Pub. No.: WO2004/054444

PCT Pub. Date: Jul. 1, 2004

(65) Prior Publication Data

US 2006/0053303 A1     Mar. 9, 2006

(30) Foreign Application Priority Data

Dec. 13, 2002   (FR) .................................. 02 15783

(51) Int. Cl.
*G06K 19/06* (2006.01)
(52) U.S. Cl. ................. 235/494; 713/185; 713/182
(58) Field of Classification Search ............... 235/494; 713/185, 182

See application file for complete search history.

(56) References Cited

U.S. PATENT DOCUMENTS

| | | | |
|---|---|---|---|
| 3,805,238 A | 4/1974 | Rothfjell | 340/146.3 |
| 4,614,366 A | 9/1986 | North et al. | 283/70 |
| 5,434,917 A * | 7/1995 | Naccache et al. | 713/176 |
| 5,839,215 A | 11/1998 | Lasprogata | 40/299.01 |
| 7,380,128 B2 * | 5/2008 | Bourrieres et al. | 713/185 |
| 2003/0014647 A1 | 1/2003 | Bourrieres | 235/61.1 |
| 2003/0154446 A1 * | 8/2003 | Constant et al. | 715/531 |
| 2005/0075984 A1 * | 4/2005 | Bourrieres et al. | 705/64 |
| 2006/0268259 A1 * | 11/2006 | Park | 356/71 |
| 2007/0023494 A1 * | 2/2007 | Haraszti et al. | 235/12 |

FOREIGN PATENT DOCUMENTS

| | | |
|---|---|---|
| EP | 0 681 252 | 11/1995 |
| GB | 2304077 A * | 3/1997 |
| GB | 2324065 A * | 10/1998 |
| WO | WO 98/02083 | 1/1998 |

OTHER PUBLICATIONS

U.S. Appl. No. 10/712,659, filed Nov. 13, 2003, Bourrieres et al.

* cited by examiner

*Primary Examiner*—Uyen-Chau N Le
(74) *Attorney, Agent, or Firm*—Vidas, Arrett & Steinkanus

(57) ABSTRACT

Identification and authentication procedure without specific reader of a three-dimensional identifier (1), (9), (10), (11) attached to an object or living being by using sensory capabilities of the human being notably its stereoscopic vision capabilities (A) and its tactile sense (A') permitting the appreciation of the particularity of the identifier which renders the latter difficult or impossible to reproduce which are, for example, heterogeneities mixed in a transparent material or surface ridges and/or cavities. The identification or reading is then carried by the visual comparison (B) of a two-dimensional representation image (2) of the identifier (1) (9) (10) (11) stored in a database (4) accessible by a network (5) and the identifier himself.

6 Claims, 3 Drawing Sheets

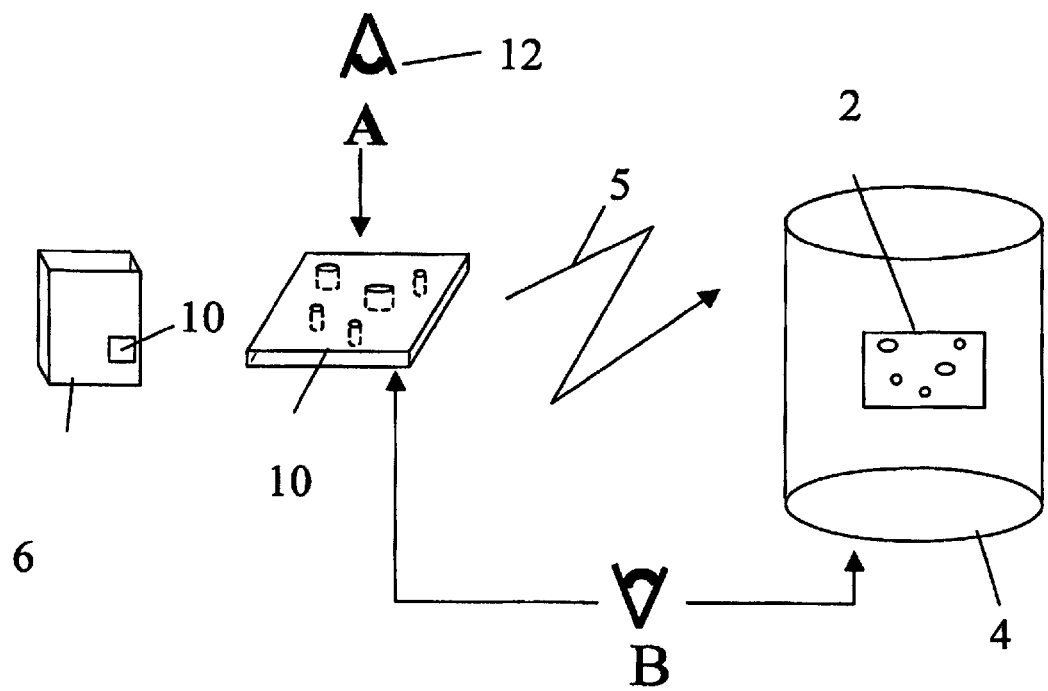
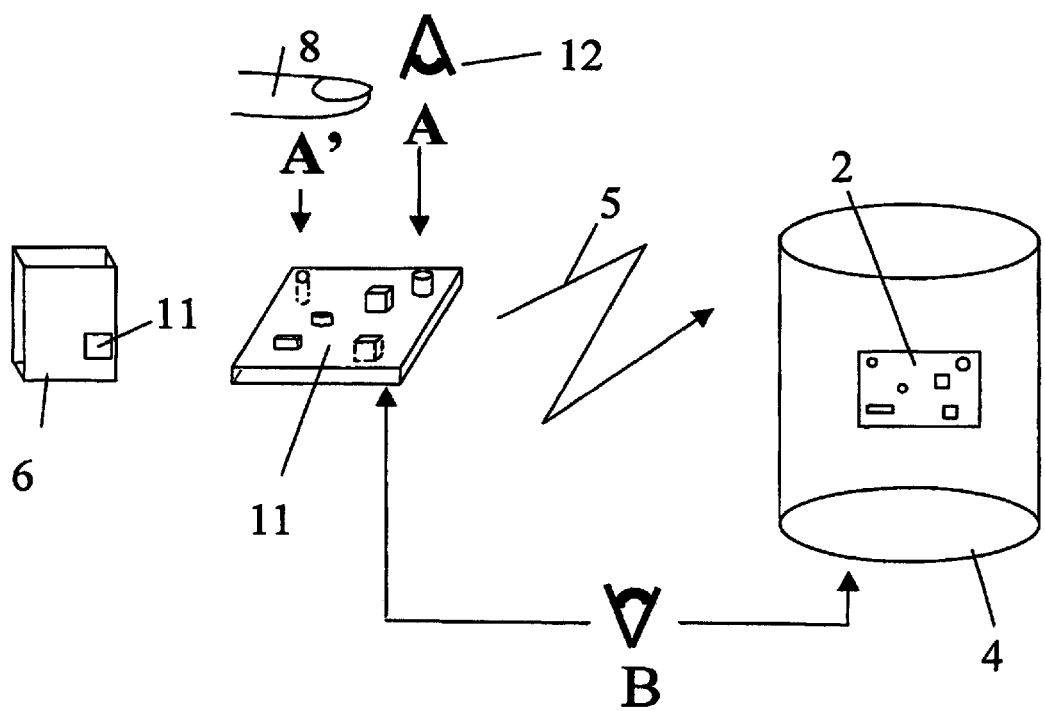

METHOD FOR IDENTIFICATION AND AUTHENTICATING WITHOUT SPECIFIC READER AN IDENTIFIER

APPLICATION DOMAIN

The present invention intends to propose a means for identifying and authenticating an identifier attached to objects or to living beings without necessitating the use of a specific reader. It will be applied in the battle against counterfeiting, traceability or security.

STATE-OF-THE-ART

These days, several means exist to identify and authenticate objects or living beings. A popular method consists in attaching a hologram to an object to be controlled as well as at the time of the transaction, the presence of a hologram is supposed to guarantee the authenticity of the product. Now with the means of reproduction and current impression, it is easy to copy and reproduce a hologram and consequently, attach a false hologram to counterfeited products. Furthermore, the buyer does not have any information a priori regarding the fact that a hologram must be present on the object and even less regarding the appearance that this hologram should have. Consequently, if the article does not show a hologram or even worse, if the latter vaguely represents the brand of the object which it is supposed to authenticate, the buyer will be duped.

Another technique consists of associating an electronic chip or a radio-frequency label called an RFID to the object to be authenticated. This solution relies upon the complexity and investment that realization of this type of identification requires as well as on shared secrets such as encrypting algorithms. This technique has two major drawbacks which considerably limit its general implementation. On the one hand, the significant cost of identifiers which is typically greater than one Euro, and on the other hand, the necessity of access to a specific reader to read and interpret the identifier.

The patent request PCT/FR01.00322 of the same inventor describes an non-reproducible identifier based upon a random distribution of heterogeneities in a transparent material. The identification and authentication of the identifier is done with the aid of a specific reader which allows the submission of the identifier to two different illuminations and of comparing the signature of the identifier presented with the one registered in the database. The necessity to use a specific reader is also a major obstacle in the extension of this technology in particular for applications to the general public.

The document U.S. Pat. No. 3,805,238 concerns an automatic or visual identification process of an individual based upon one or more particular characteristics of the person's physical appearance which have been registered in advance either in a database or directly on an item such as an identity card. The process described in this document is applied then to a person which has the particularity of presenting notable physical characteristics which may be directly used to identify the aforementioned person. In the present invention, as will be shown later on, the applicant sought to propose an indirect means of identification by proposing an identifier which is attached to an object or a living being which one wishes to label and not to identify or authenticate the object or living being itself. Consequently, the object or living being to be labeled does not necessarily have to present a notable characteristic. On the contrary, in the case of a battle against counterfeiting, the present process, the subject of the invention allows the labeling of identical objects among one another. In this regard, the inventor suggests using three-dimensional identifiers which present a random distribution of heterogeneities rendering the latter always unique and impossible or very difficult to reproduce.

The document U.S. Pat. No. 5,839,215 concerns a tactile label with the purpose of giving information about the product on which it is attached. This type of label does not have an authentication objective to the extent that they are easy to produce and reproduce identically. In no case these labels based are upon a random distribution of heterogeneities. These labels do not require comparison with an image stored in a database. In fact, this type of label has traceability as its exclusive goal but does not constitute in any manner a means of battle against counterfeiting and even less an appearance of security.

The document WO 98/02083 concerns a device and a test method of abilities or aptitudes in an automatic manner. This patent is not at all about an identification and authentication process without specific reader of an identifier attached to an object or a living being.

DESCRIPTION OF THE INVENVTION

The present invention intends to propose a human process to identify and authenticate identifiers attached to objects or living beings without the drawbacks cited above. In particular, it intends to offer a means of identification and authentication without the need of a specific reader. The innovation consists in using the options offered by modern means of communication such as the Internet or the last generation of mobile telephones which have multimedia options. To implement the invention, an identifier which is difficult or impossible to reproduce, is attached to the object or living being which one wishes to label. In a general manner, the identifier is a member of the family of three-dimensional identifiers, those which may present either a three-dimensional imprint on the surface in relief or as an imprint, or any random heterogeneous arrangement within the volume. The invention is essentially characterized by the fact that the authentication is carried out by human sensory verification of the characteristics which renders the identifier difficult or impossible to reproduce and its identification or reading is carried out by visual comparison between a two-dimensional image of the identifier stored in a database accessible by a network and the identifier himself. In this way, this invention allows the indirect recognition and identification of identical objects which is particularly new and inventive.

As a non-limiting example, it may be prudent to use three-dimensional volumic identifiers comprised of a random heterogeneous distribution in a volume made up of a transparent or translucent material. In this case and pursuant to another characteristic of the invention, the authentication is carried out by stereoscopic visual verification of the three-dimensional volumic appearance of the identifier and identification is carried out by the visual comparison of a two-dimensional representation image of the identifier, the afore-mentioned image is stored in a database accessible by a network and the identifier himself. In this case, it is a matter of advantageously using the abilities of the human eye to compare an object and its image in a related manner. If the material containing the random distribution of heterogeneities is only visible under infrared lighting, an adapted sensor placed between the eyes and the identifier will be used to visually discern if it is indeed a matter of volumic distribution.

Based upon another characteristic of the invention, in order to facilitate visual identification, one may reproduce an image similar to the two-dimensional image which is physically associated with the three-dimensional identifier. In this case, the identification is carried out by a first visual comparison between the volumic identifier and the associated similar image, then by a second visual comparison between the two-dimensional image stored in the database and the similar image. It follows that the similar image which is associated with the identifier is represented on an appropriate scale in order to facilitate the comparison. To facilitate the comparison, it may be prudent to complete the similar image and/or two-dimensional image and/or identifier with a special marking. As an example, this marking may be a lattice and/or a chart and/or orthogonal axes.

Advantageously, the present invention may be implemented by means of labels or access cards to a right or a service.

Based upon another characteristic of the invention, the network which allows access to the database is a telecommunications network.

As a non-limiting example, the access may be carried out by means of the Internet. According to another possibility, one could imagine accessing the contents of the database and in particular, a two-dimensional image which is stored there with the aid of a portable telephone with multimedial functions.

Advantageously and based upon another characteristic of the invention, the identifier may be attached in an inviolable manner to the object to be identified or authenticated.

Other characteristics of the invention will appear in reading the following figures as a non-limiting example.

FIG. 3 shows a means of verification and identification whose particularity is in presenting cavities.

FIG. 4 shows a mixed means of verification and identification whose particularity is in presenting surface ridges and cavities.

Figure 1:
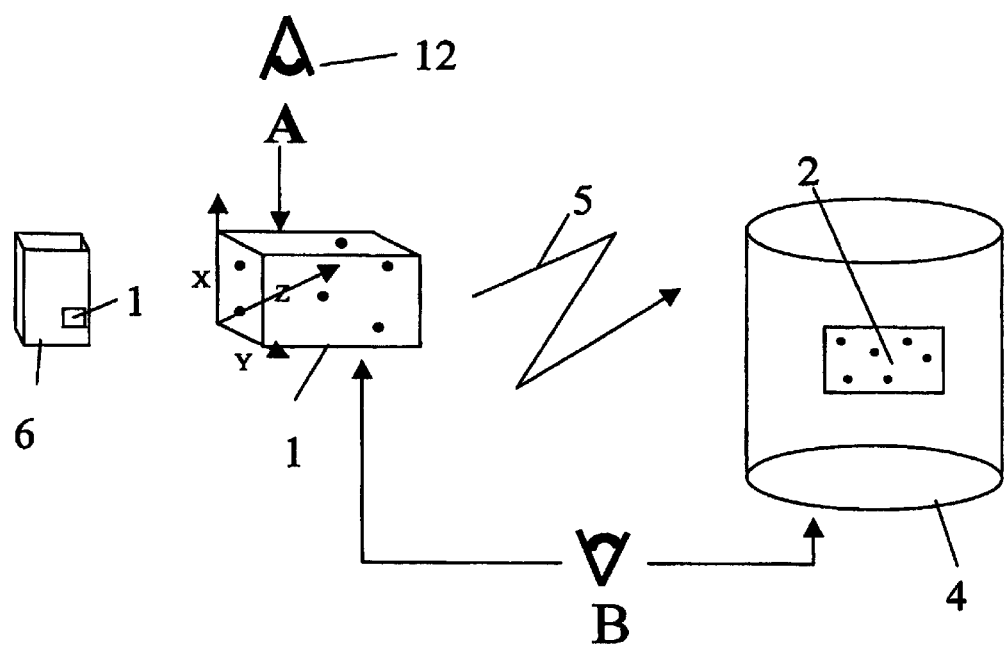
FIG. 1 shows a means of verification of an identifier whose particularity is in presenting internal heterogeneities.

FIG. 1 shows an identification and authentication process without specific reader of a volumic identifier (1) whose particularity is in presenting internal heterogeneities presenting itself in the shape of bubbles and/or solid particles distributed in a random manner within a transparent material. To verify the authenticity of the volumic distribution of the heterogeneities, one must use stereoscopic vision (A) of the human eye (12) and to proceed to identification and reading, a visual comparison (B) is carried out between the two-dimensional representation image (2) of the identifier (1) stored in the datebase (4) accessible by a network (5) and the identifier (1) himself.

Figure 2:
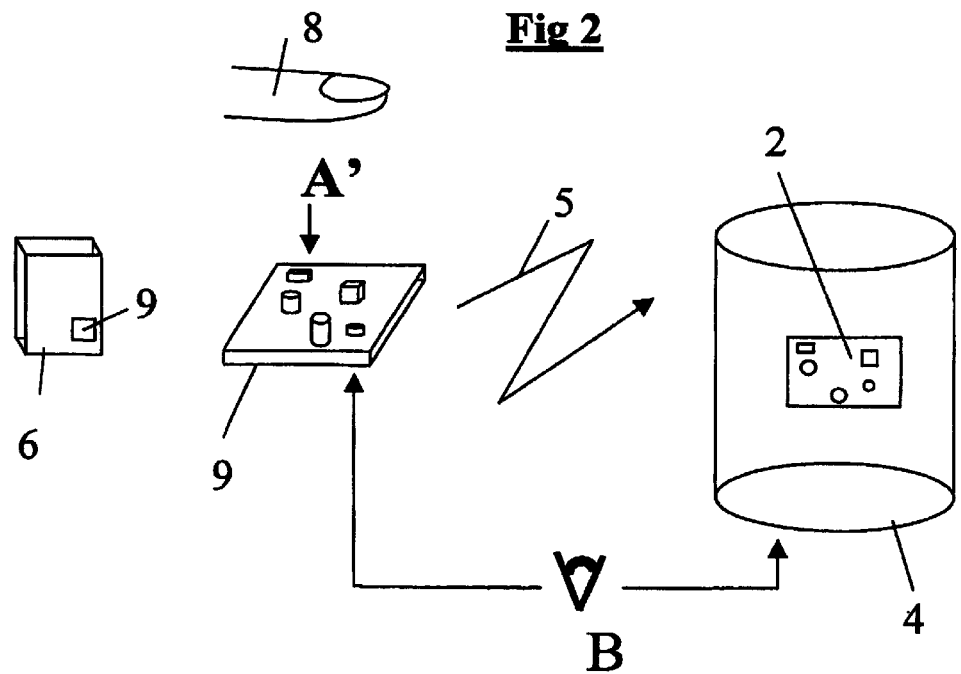
FIG. 2 shows a means of verification and identification whose particularity is of presenting surface ridges.

FIG. 2 shows an identification and authentication process without specific reader of a volumic identifier (9) whose particularity is in presenting the ridges of surfaces placed in relief. To verify the authenticity of this particularity, one uses tactile sensation (A') of a finger (8) and to proceed to the identification or reading, a visual comparison (B) is carried out between the two-dimensional representation image (2) of the identifier (1) stored in a database (4) accessible by a network (5) and the identifier (9) himself.

FIG. 3 shows an identification and authentication process without specific reader of a volumic identifier (10) whose particularity is in presenting cavities prepared from the surface of the aforementioned identifier (10). To verify the authenticity of this particularity, one uses stereoscopic vision (A) of the human eye (12) and to proceed to the identification or reading, a visual comparison (B) is carried out between the image of the two-dimensional representation (2) of the identifier (1) stored in a database (4) accessible by a network (5) and the identifier (10) himself.

FIG. 4 shows an identification and authentication process without specific reader of a mixed volumic identifier (11) whose particularity is in presenting surface ridges placed in relief and cavities prepared from the surface of the aforementioned identifier (11). To verify the authenticity of this particularity, one uses tactile sensation (A') of a finger (8) and stereoscopic vision (A) of the human eye (12) and to proceed to the identification or reading, a visual comparison (B) is carried out between the two-dimensional representation image (2) of the identifier (1) stored in a database (4) accessible by a network (5) and the identifier (11) himself.

Based upon a first means of implementation of the invention, the volumic identifier (1) (9) (10) (11) is connected to an object or a living being (6), then a two-dimensional image (2) of the identifier is registered in the database (4). The database (4) may also include complementary information such, as for example, a description, an age, a date of manufacture, a photograph, . . . of the object or living being to which the identifier is assigned. When at a later point in time, one seeks to carry out an identification and authentication of the object or living being (6) to which the identifier (1) (9) (10) (11) was assigned, one begins by carrying out sensory verification, which may be visual (A), or tactile (A') which allows in the present case authentication of where the particularities of the identifier (1) (9) (10) (11) are located. This permits the guarantee that one is dealing with an identifier and not a reproduction Then one verifies the identity of the identifier or its reading by carrying out a visual comparison (B) between the identifier (1) (9) (10) (11) and its two-dimensional image (2) stored in the database; the last being accessible by means of a network (5). It follows that if one wishes, one may first proceed to the identification without leaving the area of the present invention. Obviously to accede directly to the information authorized and corresponding to the identifier (1) (9) (10) (11) in the database (4), it is prudent to attach a call number and possibly a password to the identifier to secure access to the database. In this way, a call number corresponds to an address in the database.

Figure 5:
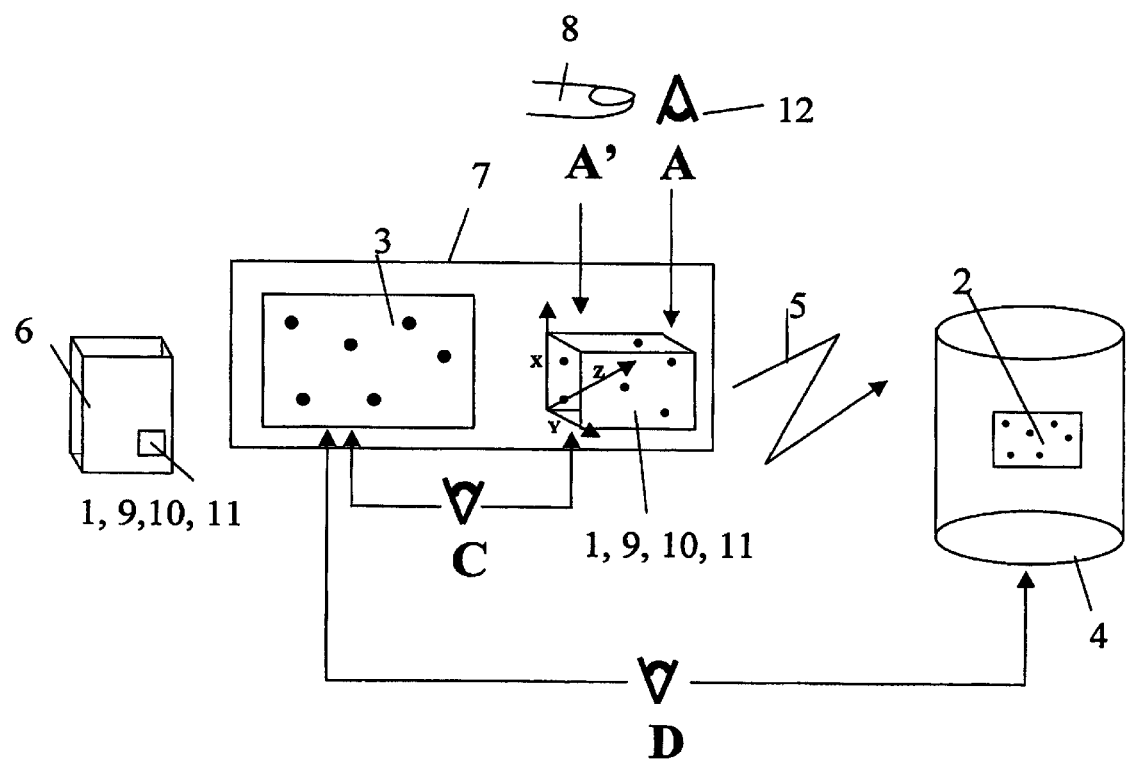
FIG. 5 shows a means of implementing the invention.

FIG. 5 shows another means to implement the present invention. In this case, the identifier (1) (9) (10) (11) is associated with a label or card (7), itself attached virtually or physically to the object or living being (6) to be identified. In the present case and in order to facilitate the identification operations, a similar image (3) showing the particularities of the identifier is printed on the label or card at an appropriate scale. In this way to proceed to a first identification, one makes a first visual comparison (C) between the identifier (1) (9) (10) (11) and the similar image (3), then a second visual comparison (D) between the similar image (3) and the two-dimensional image (2) contained in the database. For later identifications, it will suffice to proceed to the visual comparison (D) between the similar image (3) and the two-dimensional image (2).

Advantageously, the similar image (3) and the two-dimensional image (2) are at identical scales in order to facilitate their comparison.

Pursuant to another characteristic of the invention, in order to make the identifier inviolable, it may be prudent to affix upon the object to be identified in such a way so as if one seeks to detach it, one damages it irreversibly.

The present invention may be used for a large number of applications because it allows every user to access, in a very simple manner and without investment, in the verification of the authenticity of a product and its essential characteristics by simply using the sensory capacities of the human being which permits the creation of the link between a database and the identifier, difficult or impossible to reproduce, assigned to an object. It is, for example, possible to verify the biometric identities of human beings (fingerprints, iris of the eye) without having to use interpretation devices and costly readers.

The invention claimed is:

1. An identification and authentication process that is indirect and does not employ a specific reader, for identifying an object the process characterized in that:
    a three-dimensional identifier is attached to the review object, the identifier presenting three-dimensional heterogeneities distributed in a random manner within a transparent material rendering the identifier difficult or impossible to reproduce,
    the process uses stereoscopic vision (A) of the human eye (12) to verify a three-dimensional appearance and confirm the authenticity of the three-dimensional identifier (1), and
    the identification process or reading is made by visual comparison (B) of a two-dimensional first image (2) of the three-dimensional identifier (1) stored in a database (4) accessible by a network (5), to the three-dimensional identifier (1).

2. An identification and authentication process as in claim 1 wherein
    a second image (3) similar to the two-dimensional image (2) of the identifier (1) (9) (10) (11) is prepared,
    the second image (3) is physically associated with the three-dimensional identifier (1) (9) (10) (11),
    a first visual comparison (C) is carried out between the three-dimensional identifier (1) (9) (10) (11) and the second image (3),
    a second visual comparison (D) is carried out between the first image (2) and the second image (3).

3. An identification and authentication process as in claim 2 wherein the identifier (1) (9) (10) (11) and/or the two-dimensional first image (2) and/or the similar second image (3) present a particular marking or identification in order to facilitate the visual comparisons.

4. An identification and authentication process as in claim 1 wherein a call number and/or a password is associated with the identifier in order to facilitate and secure access to the database (4).

5. An identification and authentication process as in claim 1 wherein the network (5) is a telecommunications network.

6. An identification and authentication process as in claim 1 wherein the identifier (1) (9) (10) (11) and/or the two-dimensional first image (2) present a particular marking or identification in order to facilitate the visual comparison.

* * * * *